US012383425B2

United States Patent
Benkendorf et al.

(10) Patent No.: US 12,383,425 B2
(45) Date of Patent: Aug. 12, 2025

(54) CLOSURE FOR RELEASABLY SEALING AN AIR HOSE PORT

(71) Applicant: SMITHS MEDICAL ASD, INC., Plymouth, MN (US)

(72) Inventors: Gretchen Benkendorf, St. Louis Park, MN (US); Christopher Allen Lacy, Arden Hills, MN (US); Ben Peterson, Apple Valley, MN (US); Nathan L. Schlueter, Bloomington, MN (US)

(73) Assignee: ICU MEDICAL, INC., San Clemente, CA (US)

( * ) Notice: Subject to any disclaimer, the term of this patent is extended or adjusted under 35 U.S.C. 154(b) by 878 days.

(21) Appl. No.: 16/586,850

(22) Filed: Sep. 27, 2019

(65) Prior Publication Data

US 2020/0113730 A1    Apr. 16, 2020

Related U.S. Application Data

(60) Provisional application No. 62/745,673, filed on Oct. 15, 2018.

(51) Int. Cl.
*A61F 7/08* (2006.01)
*A47G 9/00* (2006.01)
(Continued)

(52) U.S. Cl.
CPC ............ *A61F 7/086* (2013.01); *A47G 9/0215* (2013.01); *A47G 9/0223* (2013.01); *A47G 2009/003* (2013.01); *A61F 2007/0055* (2013.01)

(58) Field of Classification Search
CPC . A61F 7/086; A61F 7/0097; A61F 2007/0098
See application file for complete search history.

(56) References Cited

U.S. PATENT DOCUMENTS

| 5,039,324 A | 8/1991 | Goldberg |
| 5,595,786 A * | 1/1997 | McBride, Jr. ........ C11D 17/049 |
| | | 134/40 |

(Continued)

FOREIGN PATENT DOCUMENTS

| JP | 2010013143 A | 1/2010 |
| WO | 2018075576 A1 | 4/2018 |

OTHER PUBLICATIONS

Extended EPO search report dated Mar. 22, 2022 for EP application 19872403.1.

(Continued)

*Primary Examiner* — Kaitlyn E Smith
(74) *Attorney, Agent, or Firm* — Louis Woo (57) ABSTRACT

A retainer with a closure mechanism not removable from the retainer is bonded to each of the air inlet openings of an inflatable convective thermal blanket. The bottom surface of the retainer is bonded to the blanket so that its orifice is in alignment with the opening into the blanket. The closure may be a flexible layer or sheet that is adhesively attached to the top surface of the retainer. An end portion of the flexible layer away from the orifice of the retainer may be press or die cut into the retainer so that the flexible layer is non-removably attached to the retainer when the user peels the releasably secured portion of the flexible layer away from the retainer to expose the air inlet opening. The closure can also be an extension of the retainer that is hingedly connected to the retainer so as to be able to be moved pivotally to cover the retainer. The closure has a configuration that allows it to be releasably secured to the retainer when it covers the orifice opening of the retainer.

9 Claims, 4 Drawing Sheets

(51) Int. Cl.
*A47G 9/02* (2006.01)
*A61F 7/00* (2006.01)

(56) References Cited

U.S. PATENT DOCUMENTS

| | | |
|---|---|---|
| 5,997,572 A | 12/1999 | Arnold et al. |
| 7,658,756 B2 | 2/2010 | Pierre et al. |
| 7,666,214 B2 * | 2/2010 | Pierre .................... A61F 7/0097 607/104 |
| 7,862,599 B2 | 1/2011 | Anderson |
| 8,177,828 B2 | 5/2012 | Anderson et al. |
| 9,840,346 B2 | 12/2017 | Bierschenk et al. |
| 2008/0177361 A1 | 7/2008 | Anderson |
| 2011/0022134 A1 | 1/2011 | Anderson et al. |
| 2012/0328783 A1 * | 12/2012 | Smith ........................ H02J 7/02 427/299 |
| 2014/0277307 A1 | 9/2014 | Gammons et al. |
| 2015/0121813 A1 * | 5/2015 | Bierschenk ........... B65B 9/2042 53/451 |

OTHER PUBLICATIONS

Japanese office action for JP application No. 2021-519657 dated Jun. 20, 2023.
Chinese office action and search report dated Jan. 5, 2023 for CN application 201980068'87.X.

* cited by examiner

CLOSURE FOR RELEASABLY SEALING AN AIR HOSE PORT

FIELD OF THE INVENTION

The present invention relates to convective blankets, and more particularly to a closure mechanism for the retainer bonded to an air inlet port of a convective blanket that is adapted to be used to seal the air inlet port and that, once removed, remains attached to the blanket so as to be readily available to be used to reseal the air Inlet port.

BACKGROUND OF THE INVENTION

Inflatable convective thermal blankets are well-known. An underbody convective blanket is used to support a patient and to warm the patient by outputting heated air to the patient from apertures that are formed in an upper layer of the blanket. An overbody convective blanket is used to cover a patient and similarly outputs warm air to the covered patient. The convective blankets are used mostly during surgery to prevent the patient from going into a hypothermia. Heated air is input to a convective blanket by means of at least one air inlet port formed in the blanket.

So that an air hose may be secured to the air inlet port of a convective blanket, a retainer sheet is provided at the port opening to accept the outlet nozzle of the air hose. One such retainer mechanism is disclosed in U.S. Pat. No. 7,658,756, assigned to the same assignee as the instant application. The disclosure of the '756 patent is incorporated by reference to the disclosure of the instant application. For the exemplar retainer in the '756 patent, with reference to FIG. 6, the retainer is shown to have a main body 56 and a center portion 58 demarcated by a circular cut line 60 so that the center portion can readily be removed from the retainer to expose the orifice opening into the blanket. The outlet nozzle of an air hose is then inserted past the retainer into the blanket opening. The blanket could then be inflated by the heated air input thereto via the air hose. Once removed, the center portion is usually discarded and the opening at the retainer is no longer covered, so that were a different air inlet port of the blanket to be used to accommodate a procedure on the patient, the clinician has to look for the discarded central portion and retape it back to the retainer. Given that the air hose has to be first removed from the opening and it takes time to have the opening retaped and have the center portion at the retainer of the other air inlet opening removed, precious amount of time may be wasted and a substantial amount of air would leak out of the blanket to cause possible detriment to patient. Related U.S. Pat. Nos. 6,666,879, 6,309,408, 6,241,755 and 5,997,572 each disclose an inlet port plug separate from the blanket that is shaped to fit into an open air inlet port of the blanket to block the opening. The plug can have different shapes with extensions that insert into the air inlet opening to hold the plug to the opening.

SUMMARY OF THE PRESENT INVENTION

The invention disclosed herein relates to the air Inlet or air input port of a convective blanket, and more specifically the retainer provided thereat to which the air hose for inflating the blanket is accepted or anchored. The inventive retainer has a closure mechanism attached thereto so that when the retainer is bonded to the blanket over the opening through which the nozzle of the air hose is inserted to inflate the blanket, the closure mechanisms stays with the retainer, so as to be indirectly attached to the blanket. To that end, the closure may be a flexible layer that has its surface that faces the retainer coated with an adhesive so that the layer remains attached to the retainer to act as a barrier to seal or cover the opening or orifice that is in alignment with the opening of the blanket layer(s) over which the retainer has its bottom surface bonded to. The closure may also be a sheet that has a first or main section that is bonded about the blanket opening and a second or minor section that is movably attached to the first section and can be pivoted from a position in coplanar alignment with the first section to cover the orifice opening formed in the first section. The second section is configured such that it is attached to the first section and would cover the orifice opening formed on the first section of the retainer and also be removably secured thereat.

In particular, the first embodiment of the inventive retainer and its closure mechanism has a closure that may be in the form of a flexible layer that may be a sheet, a film and/or a combination of both. The flexible layer is made from a medical grade cardboard, plastic or a polymeric material. The surface of the layer that is to be in contact with the top surface of the retainer has an adhesive coating that would attach the flexible layer to the top surface of the retainer. The adhesive for the coating is chosen to have an adhesive force that keeps the flexible layer attached to the retainer even when the convective blanket is fully inflated and the air pressure within the blanket is at maximum. The maximum pressure for an inflatable convective blanket can readily be measured and is dependent on the amount and speed of the fluid such as heated air output from an air warmer to inflate the blanket. Close to the end of the flexible layer away from the orifice of the retainer a number of pressure or die cuts may be provided to keep that end of the flexible layer pressure attached to the retainer so as not to be easily removed from the retainer when a user peels the flexible layer away from the retainer. With the removal of the portion of the flexible layer that covers the orifice of the retainer, an air hose, more specifically the nozzle thereof, can be inserted or mate to the opening of the blanket. Since the flexible layer remains attached to one end of the retainer, if the clinician be decides to use another air inlet port of the blanket for inputting air into the blanket, the orifice and therefore the opening into the blanket can be resealed by reattaching the flexible layer back to the retainer.

A second embodiment of the inventive retainer and its closure mechanism is made from one single sheet that is configured to have a retainer section and a closure section permanently but movably attached to the retainer section. A center portion of the retainer section is demarcated with a circumferential cut line so that the center portion may be punched out or removed to provide the orifice for the retainer. The retainer is bonded to the convective blanket so that orifice formed by the center portion is in alignment with the opening into the blanket, so that the air hose, more specifically its nozzle, may be inserted on or mated to the opening of the blanket. The closure section is configured to have an elongate portion and two wings extending from each longitudinal side of the elongate portion, so that the closure may have a "clover" configuration. The wings are foldable in the direction of the retainer so that they may be inserted into the orifice as the elongate portion is moved toward the retainer to cover most of the orifice opening with its rear and distal ends extending beyond the orifice to lie on top of the orifice. Given the flexibility of the wings relative to the elongate portion, once inserted into the orifice, the wings would return to their original position to act as a barrier to the remainder of the orifice opening. Given that the closure section is not permanently attached to the retainer section, the closure section can be removed from the retainer section whenever an air hose is to be inserted into the air inlet port of the blanket.

The present invention is therefore directed to a convective blanket comprising: a top layer; a bottom layer bonded to the top layer at at least the respective peripheries of the layers to form an inflatable structure; at least two openings into the structure; a retainer bonded to the structure over each of the openings, the retainer including an orifice adapted to accept an air input hose formed over and in alignment with the each opening; a closure releasably secured to each of the retainers to act as a barrier to the orifice of the each retainer to seal the opening; wherein the closure is adapted to be removed from the orifice of the each retainer to enable the air hose to be inserted through the orifice of the each retainer into the each opening, a portion of the closure away from the orifice being non-removably attached to the retainer; and wherein the closure is further adapted to be releasably secured to the each retainer to act as a barrier to the orifice of the each retainer after the air hose is removed from the each opening.

The present invention is further directed to an inflatable blanket comprising: a top layer and a bottom layer bonded together with each other at their respective peripheries to form an inflatable structure; at least one opening into the structure adapted to accept an air hose; a retainer having a bottom surface bonded to the structure over the one opening, the retainer including a top surface and an orifice formed over and in alignment with the one opening; a closure non-removably attached to the retainer including a surface configured to releasably secure the closure to the retainer to close the orifice and seal the one opening, the closure adapted to be removed from the orifice of the retainer while remaining attached to the retainer to enable the air hose to be mated to the orifice and the one opening, the closure further adapted to be releasably resecured to the retainer to close the orifice and reseal the one opening after the air hose is removed from the one opening and the orifice.

The present invention is yet further directed to a method of manufacturing an inflatable blanket, comprising the steps of:
 bonding a top layer and a bottom layer together at least at their respective peripheries to form an inflatable structure;
 providing at least one opening adapted to accept an air hose into the structure;
 bonding a bottom surface of a retainer to the structure over the one opening, said retainer including a top surface and an orifice adapted to the accept an air hose formed over and in alignment with the one opening;
 non-removably attaching a closure to said retainer;
 configuring a surface of said closure to releasably secure said closure to said retainer to close the orifice and seal the one opening; and
 configuring said closure to be removable from the orifice of said retainer while remaining attached to said retainer to enable the air hose to be mated to the orifice and the one opening, said closure further configured to be releasably resecured to said retainer to close the orifice and reseal the one opening after the air hose is removed from the one opening and the orifice.

BRIEF DESCRIPTION OF THE FIGURES

The present invention will become apparent and will best be understood by reference to the following description of the invention taken in conjunction with the accompanying drawings, wherein.

DETAILED DESCRIPTION OF THE INVENTION

Figure 1:
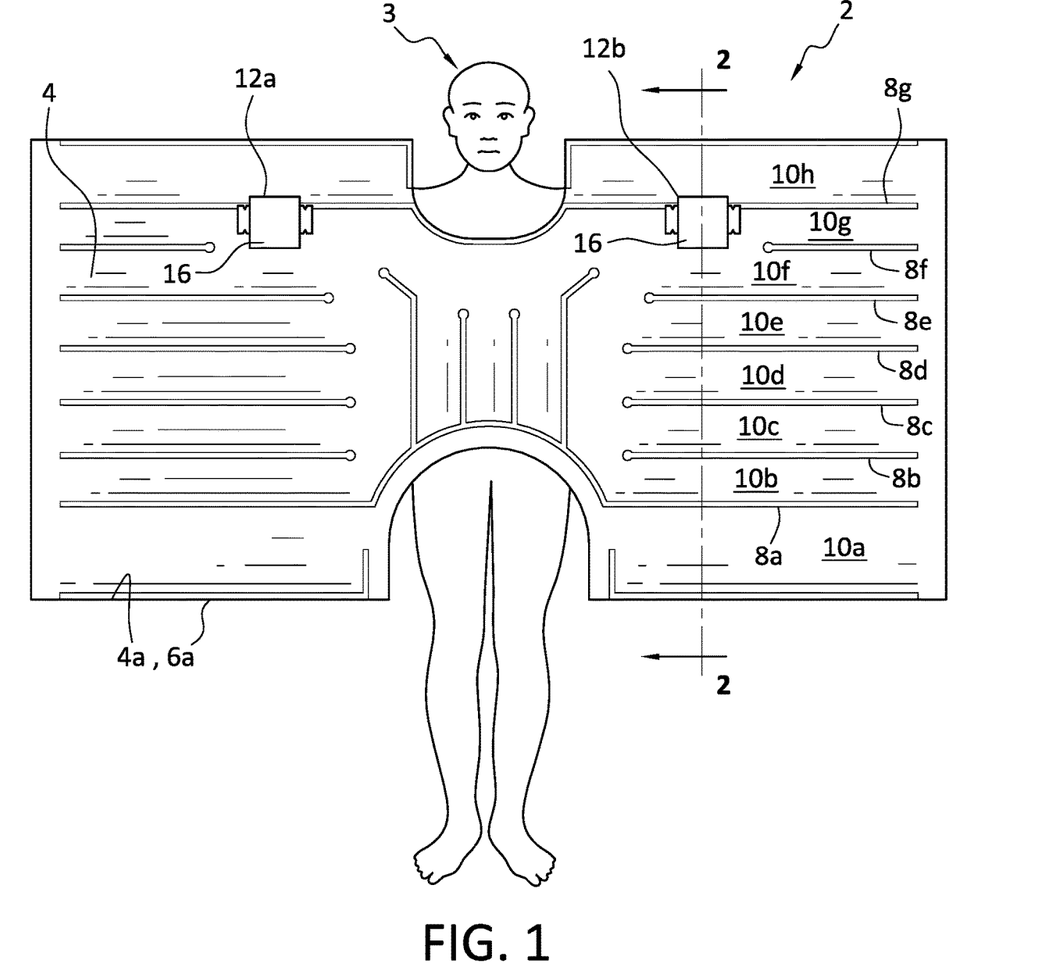
FIG. 1 is a top view of an exemplar inventive blanket shown placed over a patient.
Figure 2:
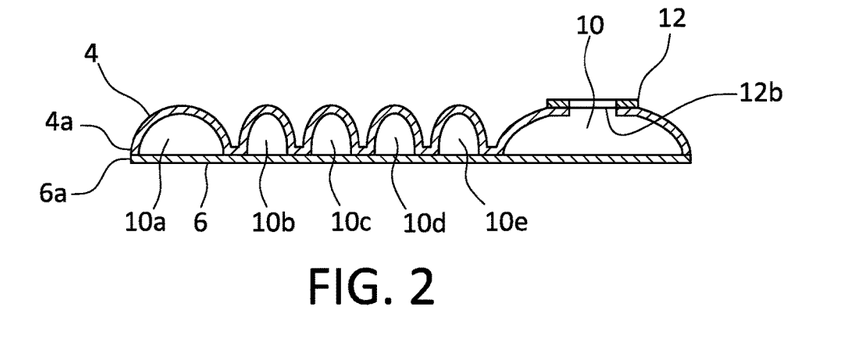
FIG. 2 is a cross sectional view of the blanket of FIG. 1 along section line 2-2.

With reference to FIG. 1, a convective blanket 2 with the inventive retainer and closure mechanism is shown. As is known, a convective warming blanket such as that shown in FIG. 1 has a first or upper layer and a second or lower layer bonded at least at their respective peripheries to form an inflatable structure. FIG. 2 shows, per the cross-sectional view of blanket 2 along a sectional line 2-2 in FIG. 1, the upper layer 4 and lower layer 6 of the inflatable blanket and their respective peripheries 4a and 6a. A number of seals 8a-8g in blanket 2 partition the blanket into a number of inflated tubes 10a-10h, when air is input to the blanket via input port opening 10 to inflate the blanket. As shown in FIG. 1, the seals throughout the blanket are arranged such that passageways are provided among the seals so that fluid such as air input into the blanket to inflate the blanket would circulate throughout the blanket. Although not shown, the layer of the blanket that comes into contact with the patient 3 has a plurality of apertures so that the heated air input into the blanket to inflate the blanket would exit through the apertures to warm the patient. For the overbody blanket shown in FIG. 1, the apertures are provided in the bottom layer of the blanket. For an underbody blanket onto which a patient is placed, the apertures are provided on the upper layer of the blanket to warm the patient lying thereon.

For the blanket shown in FIG. 1, there are two openings provided at the upper layer 4 of the blanket. Each of the openings 10 has a retainer 12 bonded to the surrounding area of the opening at the upper layer 4 of the blanket. Although there are two retainers 12 shown in the exemplar blanket of FIG. 1, it should be appreciated that there may be only one, or more than two openings and their corresponding retainers provided on a convective blanket. One reason that multiple openings are provided in a blanket is a surgeon may need to perform procedure(s) on a patient at different positions relative to the patient, with the blanket being continually placed over/under the patient during the procedure. Point of illustration. If the surgeon needs to operate on a patient from the patient's right side, with reference to the patient 3 shown in FIG. 1, the air hose would need to be inserted into the blanket by way of the opening at retainers 12. If the surgeon then needs to operate on the patient from his left side, then the opening at retainer 12b has to be closed off, after the air hose has been removed therefrom. Thereafter, the air hose is inserted into the opening at the retainer 12a so that the air hose would not get in the way of the surgeon. Another reason is that air warmers for inputting air into convective blankets have their air hoses at different locations, depending on the air warmer. Therefore, it may be more expedient to connect the air hose from one particular air warmer to a given opening on the blanket and connect the air hose from another particular air warmer to another opening on the blanket.

Figures 3, 4, 5:
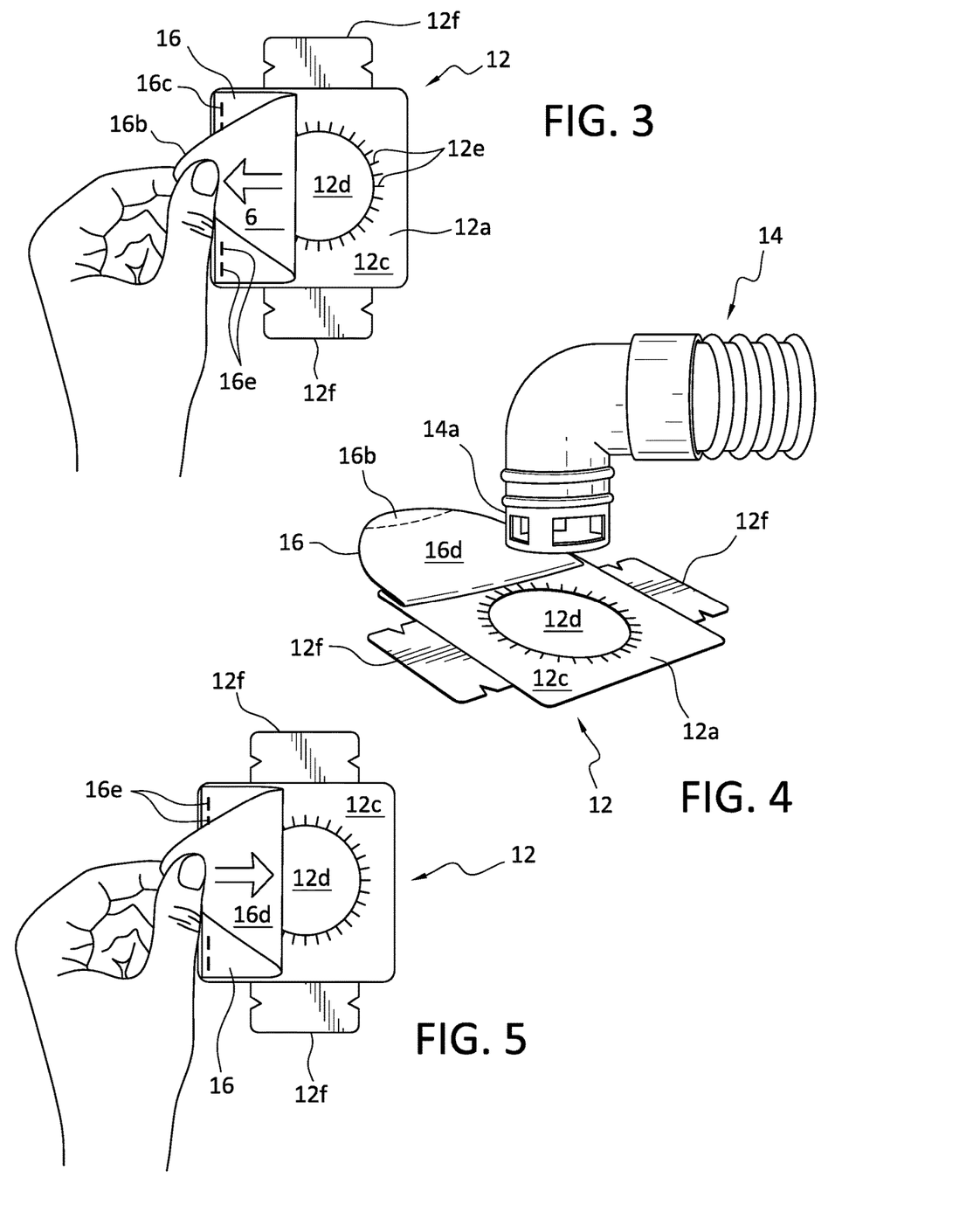
FIG. 3 is an illustration of a first embodiment of the retainer of the blanket of the instant invention.
FIG. 4 is an illustration of the inventive retainer shown in FIG. 3 where the portion of the closure covering the orifice of the retainer has been removed so that an air hose may be inserted through the orifice into the air inlet opening of the blanket.
FIG. 5 is an illustration showing the resealing of the orifice of the retainer after the air hose has been removed from an inlet port of the blanket.

A first embodiment of the inventive retainer and its closure mechanism is shown in FIG. 3. As shown, a retainer 12 has a top surface 12c and a bottom surface 12b (FIG. 2) that is bonded, by any of the conventionally known methods, to the upper layer 4 of the blanket 2 shown in FIG. 1. The retainer 12 is shown to have a main body 12a with an orifice opening or orifice 12d at substantially the center of the main body. A number of cut lines 12e are provided around orifice 12d to enable an air hose 14 (FIG. 4), more precisely the nozzle 14a of the air hose, to be inserted into orifice opening 12d, which for the sake of ease of discussion, should be considered the same as the opening 10 into the blanket. Thus, the terms orifice or orifice opening should be considered the same as the opening into the blanket. The retainer acts to anchor or retain the air hose to the blanket opening 10. There are two flaps or wings 12f extending from opposite sides of main section 12a of retainer 12. The flaps 12f may be bent upwardly from main section 12a for attachment with corresponding tabs (not shown) that may be mounted to an air hose. The retaining of an air hose by a retainer may be gleaned from FIGS. 9 and 10 of the above-noted incorporated by reference '756 patent. The retainer 12 may be a sheet made from a medical grade cardboard, or plastic, or some other material that would afford flexibility and bendability.

A closure 16 may be a flexible layer or sheet or a film layer formed from a flexible medical cardboard or plastic material or polymeric material including polypropylene, polyethylene, cellophane, or any other polymeric material suitable for forming a releasable and resealable cover for the orifice 12d of retainer 12. For ease of discussion, the terms closure, flexible layer, thin layer or cover for the retainer may be used interchangeably in the remainder of the disclosure of this application.

As shown in FIG. 3, flexible layer 16 has a dimension that allows it to substantially cover the main section 12a of retainer 12. The portion of the flexible layer 16 shown to be held by the thumb and the forefinger of the hand in FIG. 3 may be referred to as a tab 16b. Away from the tab 16b and extending to the rear end 16c of the flexible layer, the surface of the flexible layer that contacts the upper top surface 12c of retainer 12 is coated with an adhesive so that there is an adhesive coating at surface 16d of flexible layer 16 that comes into contact with the top surface 12c of retainer 12. A number of press or pressure cuts or die cuts 16e are provided near the rear end 16c of the flexible layer 16 into the main section 12a of retainer 12. The die cuts 16e, resulting in portions of the flexible layer being pressed into the main section 12a of the retainer 12, act to prevent a user from accidentally over peeling the flexible layer of the retainer. In other words, the die cuts 16e ensure that the flexible layer 16 is non-removably attached to retainer 12.

The adhesive coated to surface 16d of the flexible layer 16 may be any known adhesive in the art which, advantageously, has a bond strength that maintains the flexible layer or closure adhesively secured to the retainer in reaction to the air pressure inside the structure even when the structure is fully inflated, i.e., have enough bond strength to withstand the pressure force exerted by the air in a fully inflated structure. But the bond strength of the adhesive coating is such that the portion of the closure that covers the orifice can be separated from the retainer by the user applying at least a predetermined peeling force that peels the closure away from the retainer. The maximum air pressure that a convective thermal blanket can withstand, and therefore exerted against the closure, is conventionally known since it is a design feature that has to be taken into account for the manufacturing of each type of convective blanket. FIG. 3 shows the user peeling a portion of the closure 16 away from the top surface 12c of retainer 12 to expose orifice 12d in preparation for the mating of air hose 14 into the opening of the blanket. As shown in the exemplar blanket of FIG. 1, before use, the retainers 12 are covered by the closures 16.

FIG. 4 shows the nozzle 14a of the air hose 14 being inserted or mated through orifice 12d into the opening of the blanket, after the closure or flexible layer 16 has been peeled back to a position that allows air hose 14 to be mated to orifice opening 12d.

FIG. 5 shows the user resealing orifice 12d, after the air hose has been removed from the orifice 12d of the retainer 12 and therefore from the opening of the blanket, by reattaching the adhesive coated surface 16d of the closure flexible layer 16 onto the top surface 12c of the retainer 12. Such resealing of the retainer allows the clinician to matingly attach the air hose to another air input port of the blanket in the event that a repositioning of the clinician vis-a-vis the patient is needed, as per discussion above.

Figure 6:
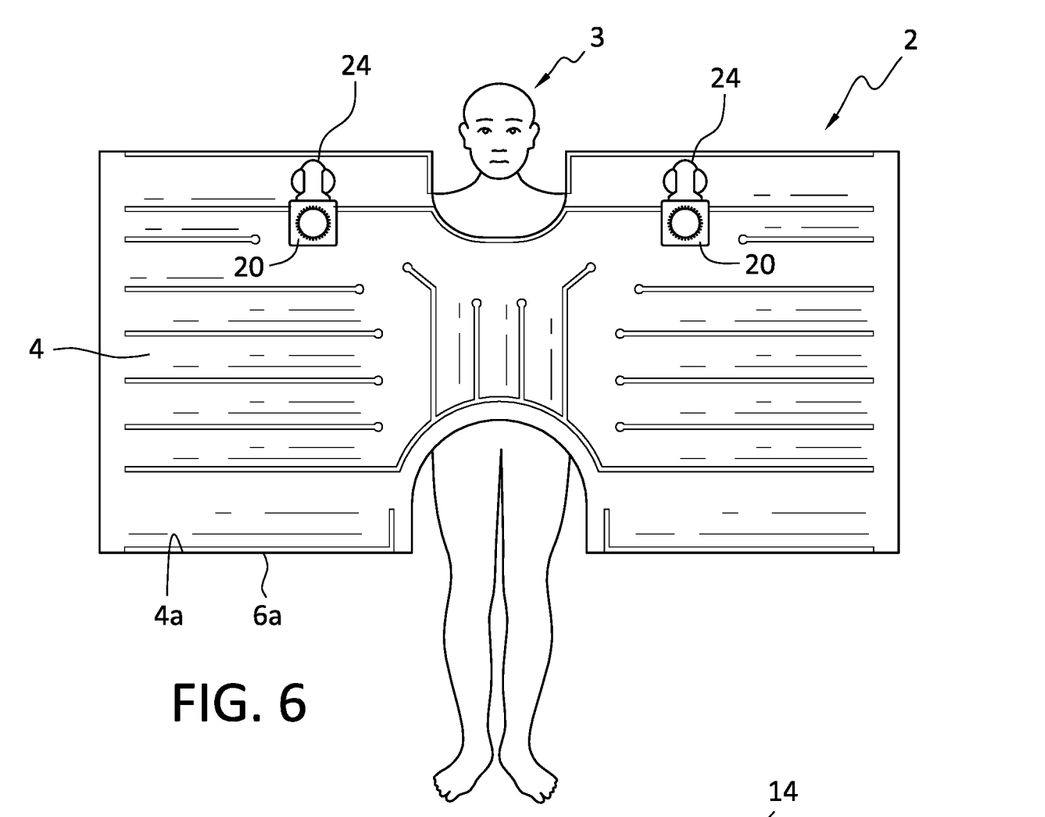
FIG. 6 is a top few of another exemplar inventive blanket shown placed over a patient.

A second embodiment of the retainer of the instant invention is attached to the exemplar blanket 2 shown in FIG. 6. Except for the retainer and its closure, the exemplar blanket shown in FIG. 6 is identical to the blanket shown in FIG. 1. Accordingly, the same number designations are used for the same components or elements shown in those figures. It should be appreciated that the inventive retainer and closure are adapted to be used in blankets of different sizes and dimensions, as well as different configurations, and are therefore not limited to be used only with the exemplar overbody blanket shown in FIGS. 1 and 6.

Figure 7:
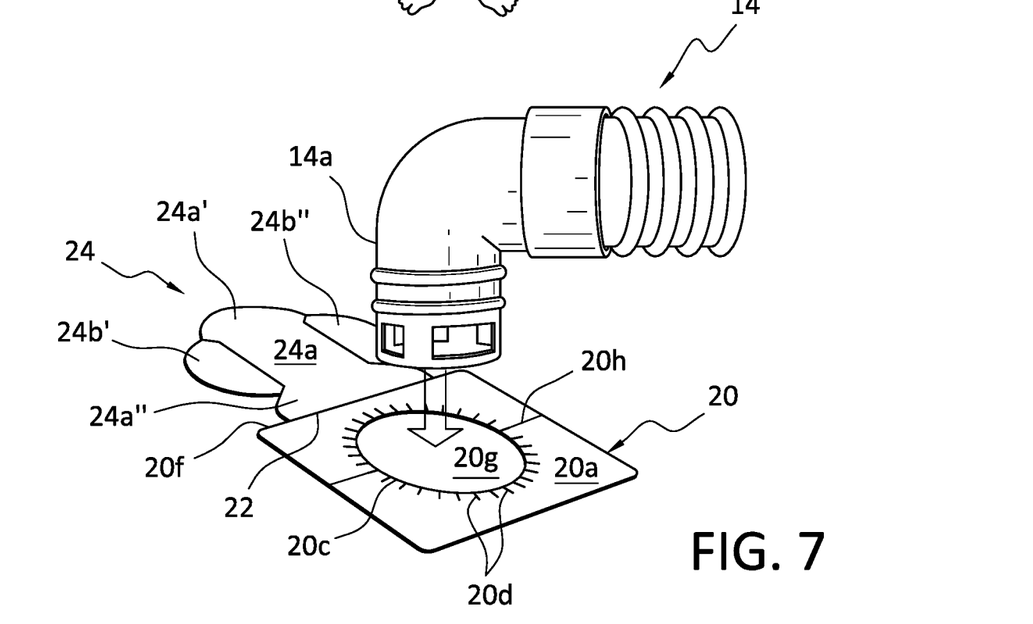
FIG. 7 shows a second embodiment of the inventive retainer and closure for accepting an air hose into the orifice of the retainer.

The retainer and closure embodiment shown in FIG. 7 has a retainer 20 that may also be made from a sheet of medical grade cardboard, plastic, or some other material that affords flexibility and bendability. Retainer 20 has a top surface 20a and a bottom surface, not shown, that is bonded to the area of the layer of the blanket that has the opening, the same as the embodiment retainer shown in FIG. 2. Before use, the retainer 20 may have a center portion formed by a cut line 20c at substantially the center of the retainer. As with the first embodiment retainer, a plurality of cut lines 20d are provided about center portion to facilitate the insertion and the holding of the air hose nozzle to the retainer once the center portion has been removed from the retainer and the air hose nozzle inserted into the orifice opening created by the removal of center portion. Alternatively, the center portion may be removed before the blanket is shipped so that there's no need to remove the center portion from retainer 20 before use. For the discussion below, it is assumed that the center portion has been removed from the retainer 20 and that the center of retainer 20 shown in FIG. 7 is an orifice opening 20g. A fold line 20h extends across the main body of retainer 20 to enable the retainer to be folded to accommodate the bonding of the retainer to corresponding edges of the upper and lower layers of those blankets that require the retainer to be thus bonded. One such edge bonding of the retainer may be gleaned from FIG. 5 of the above incorporated by reference '756 patent.

Figure 8:
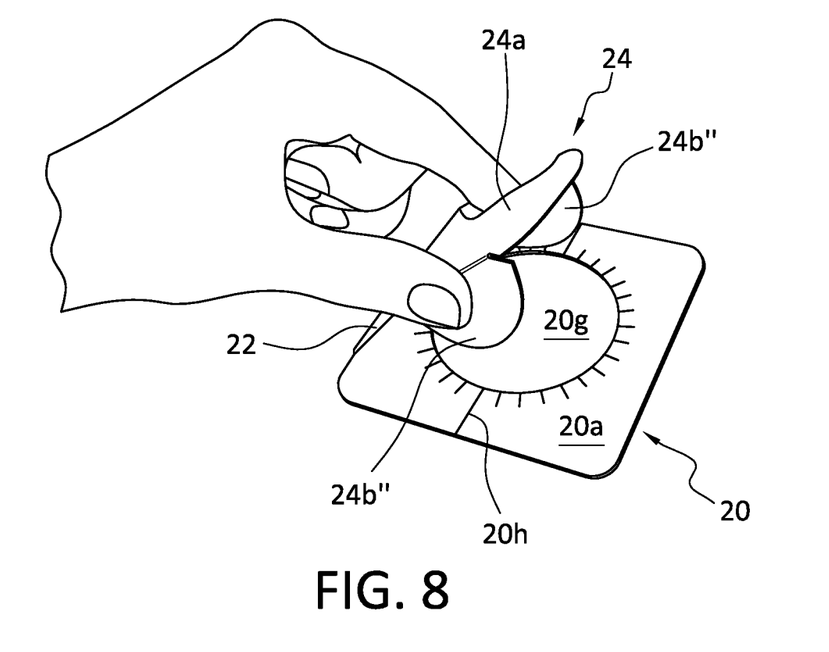
FIG. 8 is an illustration showing the closing of the orifice of the retainer by its attached closure.
Figure 9:
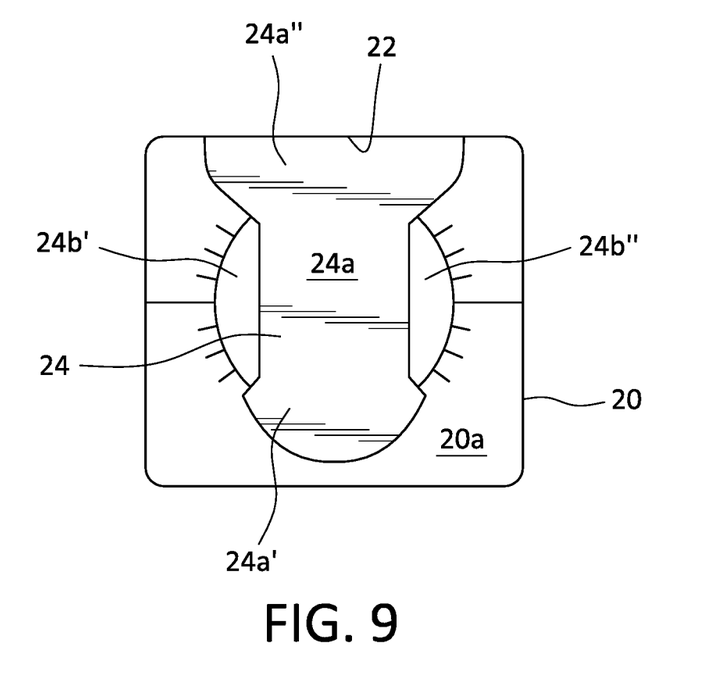
FIG. 9 shows the inventive retainer having his orifice sealed by the closure.

Attached to an edge 20f of retainer 20, by means of a hinge line 22, is a closure 24. Since closure 24 is an extension of retainer 20, it likewise may be a sheet made of the same material as the retainer. As shown in FIGS. 7-9, closure 24 has an elongate portion 24a that extends from the hinge lined 22. Elongate portion 24a has a semicircular head portion 24a' and an enlarged rear portion 24a" pivotally connected to the retainer edge 20f via hinge line 22. Extending from the longitudinal sides of the elongate portion 24a are semicircular wings 24b' and 24b" that are foldable along the respective longitudinal sides relative to the elongate portion 24a towards the orifice 20g, as per shown in FIG. 8. Thus, the retainer of the embodiment shown in FIG. 7 may be considered to be a sheet having a main section that is retainer 20 and a minor section that is the closure 24.

FIG. 7 shows an air hose 14 being inserted into the orifice opening 20g and therefore into the air inlet opening of the convective blanket to inflate the blanket. The nozzle 14a of the air hose 14 will be retained by the retainer 20, specifically by the circumferential inwardly pointing edges with the multiple cut lines 20d that surround the orifice opening 20g. When the air hose is mated to the retainer, closure 24 remains in coplanar alignment with retainer 20, as closure 24 is an extension of retainer 20.

FIG. 8 is an illustration showing the sealing of orifice opening 20g by closure 24, after the air hose 14 has been removed from the orifice opening 20g of retainer 20. One possible reason that orifice 20g needs to be closed off to the environment is that the clinician wants to have the air hose inserted into another air input port of the blanket to inflate the blanket. Another reason is that the clinician may want the blanket to be fully inflated, notwithstanding the air being output from the apertures at the layer of the blanket that contacts the patient, to another location of the patient or cover another body part of the patient, before reconnecting the air hose to the blanket. As shown, the clinician is pressedly holding the wings 24b' and 24b" of closure 24 with her thumb and index finger so that the wings are folded toward the retainer 20 for insertion into orifice 20g.

As shown in FIG. 9, once inserted into orifice 20g, wings 24b' and 24b" will return to their original position while at the same time the elongate portion 24a lies over orifice 20g with its semicircular head portion 24a' extending beyond the edge of orifice opening 20g to rest on the top surface 20a of retainer 20. With the wings 24b' and 24b" returning to their original position and elongate portion 24a resting on the top surface 24a' of the retainer 20, the orifice opening 20g is sealed by closure 24 and securely held thereto by rear portion 24a" and the head portion 24a' resting onto the top surface 20a and the wings 24b' and 24b" upwardly pressing against the underside of retainer 20. Using the head portion 24a' as a tab, a user can remove closure 24 from retainer 20 with an upward peeling motion.

There are a number of advantages the retainer and closure mechanism of the instant invention has over the prior art. First, the sealing of the orifice opening of the retainer can be done with a one-handed operation by merely pivoting the closure to cover the retainer. In contrast, for the above discussed port plug in the '879 patent, more likely than not, a two-handed operation is required to hold, fold and insert the plug into the opening of the retainer. Second, keeping a surgical access blanket inflated while the hose is disconnected from one air input port and connected to another air input port allows the surgeon or clinician to maintain his view of the area around where he or she is working. This is advantageous because the surgeons often wear magnifying glasses during surgery and their depth and peripheral vision images are important. Third, oftentimes a closure separate from the retainer such as the port plug discussed above is discarded or is lost for example during surgery or when the patient is transported to a to different locations or room that has an air blower with a different air hose location. In those instances, the old blanket needs to be thrown out and replaced with a new blanket.

The invention disclosed above is subject to many variations, modifications and changes in detail. For example, for the embodiment of FIGS. 1-5, instead of having the adhesive coating on the surface of the flexible layer that comes into contact with the retainer, the adhesive may be coated onto the surface of the retainer that the flexible layer comes into contact with so that the flexible layer, acting as the closure of the opening at the retainer, is releasably secured to the retainer. Same as discussed above, the flexible layer is removable from the orifice of the retainer by the user applying a force sufficient to peel the flexible layer away from the adhesive coated surface of the retainer. Thus, it is intended that all matters described throughout this specification and shown in the accompanying drawings be interpreted as illustrative only and not in a limiting sense. Accordingly, it is intended that the invention be limited only by the spirit and scope of the hereto attached claims.

The invention claimed is:

1. A convective blanket adapted to be inflated by air input therein from an air warmer, comprising:
   a top layer;
   a bottom layer bonded to the top layer at at least the respective peripheries of the layers to form an inflatable structure;
   at least two openings into the top layer of the structure;
   a retainer bonded to the top layer of the structure over each of the openings, the retainer including an orifice having a number of cut lines provided around the orifice to enable a nozzle of an air hose connected to the air warmer to be inserted into the orifice in alignment with the opening;
   a closure overlying the retainer having an end portion non-releasably attached to the retainer, a barrier portion of the closure releasably securable to the portion of the retainer that includes the orifice to cover the opening when the barrier portion is secured to the retainer;
   wherein the barrier portion of the closure covering the opening is removable from the retainer to allow the nozzle of the air hose to be inserted through the orifice of the retainer into the opening while the closure remains attached to the retainer;
   wherein the barrier portion of the closure is adapted to be resecured to the retainer to cover the opening after the nozzle of the air hose is removed from the opening; and
   wherein the end portion of the closure is pressed into the retainer by a number of die cuts, and wherein the barrier portion of the closure has an adhesive coated on the surface of the barrier portion that comes into contact with the retainer to releasably secure the barrier portion of the closure to the retainer to seal the orifice to close the opening, the closure including a tab to enable a user to remove the barrier portion of the closure from the retainer with a peeling motion while the closure remains attached to the retainer.

2. The blanket of claim 1, wherein the closure comprises a flexible layer that may be formed from polypropylene, polyethylene, cellophane, or any other polymeric material suitable for forming a releasably resealable cover for the orifice of the retainer.

3. The blanket of claim 1, wherein the retainer comprises a sheet made of cardboard, plastic or a material that is flexible and bendable and wherein the closure comprises a flexible thin layer adapted to be removably attached to the retainer.

4. An inflatable blanket comprising:
a top layer and a bottom layer bonded together at least at their respective peripheries to form an inflatable structure;
at least one opening provided at the top layer into the structure adapted to accept an air hose;
a retainer having a bottom surface bonded to the top layer of the structure over the opening, the retainer including a top surface and an orifice having a number of cut lines provided around the orifice formed over and in alignment with the opening to accept a nozzle of the air hose;
a closure overlying the retainer having an end portion non-releasably attached to the retainer, a barrier portion of the closure releasably securable to the portion of the retainer that includes the orifice to cover the opening when the barrier portion is secured to the retainer, the barrier portion of the closure is removed from the retainer to allow the nozzle of the air hose to be inserted through the orifice of the retainer into the opening while the closure remains attached to the retainer, the barrier portion of the closure is adapted to be resecured to the retainer to cover the opening after the nozzle of the air hose is removed from the opening;
wherein the end portion of the closure is attached to the retainer by a number of die cuts;
wherein an adhesive coating at the bottom surface of the barrier portion to contact the retainer or the top surface of the retainer to contact the barrier portion adapted to releasably secure the barrier portion and the retainer to each other to cover the orifice; and
wherein the closure includes a tab to enable a user to remove the barrier portion from the retainer with a peeling motion.

5. The blanket of claim 4, wherein the closure is secured to the retainer with a sufficient holding force to prevent the internal pressure of air in the structure, when the structure is fully inflated, to separate the closure from the retainer, the barrier portion of the closure removable from the retainer by a user applying a force greater than the holding force to peel the barrier portion away from the top surface of the retainer.

6. The blanket of claim 4, wherein the closure comprises a flexible layer that may be formed from polypropylene, polyethylene, cellophane, or any other polymeric material suitable for forming a releasably resealable cover for the orifice of the retainer.

7. A method of manufacturing an inflatable blanket, comprising the steps of:
bonding a top layer and a bottom layer together at least at their respective peripheries to form an inflatable structure;
providing at least one opening at the top layer adapted to accept an air hose into the structure;
bonding a bottom surface of a retainer to the top layer over the opening, the retainer including a top surface and an orifice adapted to accept an air hose formed over and in alignment with the opening;
overlaying a closure over the retainer;
non-removably attaching an end portion of the closure to the retainer;
overlaying a barrier portion of the closure configured to close the orifice and seal the opening over the orifice of the retainer;
configuring the barrier portion of the closure to be releasably securable to the retainer, the retainer having a number of cut lines provided around the orifice to enable a nozzle of the air hose to be mated to the orifice and into the opening, the barrier portion of the closure releasably resecured to the retainer to close the orifice and reseal the opening after the air hose is removed from the opening and the orifice; and
attaching the end portion of the closure to the retainer by a number of die cuts;
providing the adhesive coating at the surface of either the barrier portion of the retainer or the retainer with sufficient holding force to prevent the internal pressure of air in the structure, when the structure is fully inflated, to separate the closure from the retainer, the closure removable from the orifice of the retainer by a user applying a force greater than the holding force to peel the barrier portion of the closure away from the retainer.

8. The method of claim 7, further comprising the steps of:
providing the adhesive coating to the surface of the barrier portion of the closure that comes into contact with the retainer to close the orifice of the retainer; and
forming a tab to the closure to enable a user to remove the barrier portion of the closure from the retainer with a peeling motion.

9. The method of claim 7, further comprising the steps of:
providing the closure as a flexible layer that releasably covers the orifice of the retainer; and
forming the flexible layer from polypropylene, polyethylene, cellophane, or any other suitable polymeric material.

* * * * *